United States Patent [19]

Mitchell

[11] Patent Number: 5,024,664
[45] Date of Patent: Jun. 18, 1991

[54] VACUUM INFUSION DEVICE

[75] Inventor: Richard J. Mitchell, Lindenhurst, Ill.

[73] Assignee: Baxter International Inc., Deerfield, Ill.

[21] Appl. No.: 514,799

[22] Filed: Apr. 26, 1990

[51] Int. Cl.$^5$ ............................................. A61M 31/00
[52] U.S. Cl. ...................................... 604/143; 604/131
[58] Field of Search ............... 604/140, 141, 143, 144, 604/146, 147, 131, 142, 145, 149; 222/389

[56] References Cited

U.S. PATENT DOCUMENTS

| | | | |
|---|---|---|---|
| 3,349,767 | 10/1967 | Gidlund | 640/143 |
| 3,727,614 | 4/1973 | Kniazuk . | |
| 4,022,209 | 5/1977 | Nehring . | |
| 4,036,232 | 7/1977 | Genese . | |
| 4,180,067 | 12/1979 | Derlien | 604/131 |
| 4,212,298 | 7/1980 | Gezari | 604/121 |
| 4,303,376 | 12/1981 | Siekmann | 417/360 |
| 4,560,979 | 12/1985 | Rosskopf | 604/131 |
| 4,666,430 | 5/1987 | Brown et al. | 604/141 |
| 4,765,509 | 8/1988 | Eisenhut et al. | 222/389 |
| 4,773,900 | 9/1988 | Cochran | 604/143 |
| 4,813,937 | 3/1989 | Vaillancourt | 604/131 |

Primary Examiner—Paul J. Hirsch
Attorney, Agent, or Firm—Paul E. Schaafsma; Amy L. H. Rockwell; Paul C. Flattery

[57] ABSTRACT

A vacuum biased disposable infuser is provided having a liquid chamber (14) and at least one vacuum chamber (44). The liquid chamber (14) includes a liquid plunger (26) contained therein while the vacuum chamber (44) includes a vacuum plunger (48). The plungers (26, 48) are connected by an arm such that when liquid under pressure is provided to the liquid chamber (14), the vacuum plunger (48) is drawn back in the vacuum chamber (44). The device is further preloaded such that at the end of infusion, the vacuum plunger (48) does not abut against the vacuum chamber (44).

10 Claims, 3 Drawing Sheets

VACUUM INFUSION DEVICE

FIELD OF THE INVENTION

The present invention relates to the controlled delivery of liquids and, in particular, to portable apparatus for delivery of a medical liquid having a beneficial agent to a patient.

BACKGROUND OF THE INVENTION

Devices for infusing to a patient a beneficial agent such as a drug diffused in a medical liquid are known in the art. The most common device utilizes an elevated glass or flexible container having a beneficial agent diffused in a medical liquid which is fed by gravity to a patient's venous system via a length of flexible plastic tubing and a catheter. The rate of flow in this type of device is commonly regulated by an adjustable clamp on the tubing. This set-up suffers from the drawback of requiring a relatively stationary patient and is dependent on the height differential between the medical liquid and the patient for accurate delivery rates.

An additional type of infusion device utilizes electromechanical components and a pump to provide fluid propulsion of the medical liquid for infusion into the patient. Such electronically controlled infusion devices, however, suffer from several drawbacks, including the cost of such electrical components as well as the limit such electrical components and the necessary power source place on the size and thus portability of the device.

Devices in the art are also utilized which employ an elastomeric bladder which contains the medical liquid to be infused under pressure for infusion. A typical elastomeric bladder device includes housing, a plug fixed in one end of the housing which includes aperture that extends through the plug, and a tubular elastomeric bladder in the housing for receiving the liquid under pressure. One end of the bladder is sealingly attached to the plug, with the interior of the bladder communicating with the aperture of the plug. A conduit connected to the plug aperture defines with the aperture a dispensing passageway for transporting the medical liquid from the bladder to the infusion site of the patient. A flow regulator is disposed somewhere in the dispensing passageway for permitting the medical liquid to flow from the bladder to the dispensing passageway at a predetermined rate into the patient.

Another type of device utilizes a syringe-type construction having a plunger disposed within and making sliding, sealing contact with the interior surface of the syringe barrel. A biasing means such as a spring or an elastomeric band is also provided between the plunger and the housing. Medical liquid to be infused is received under pressure within the interior of the barrel in a chamber defined by the interior of the barrel and the plunger. The pressurized medical liquid forces the plunger to bias the biasing member thereby providing a source of medical liquid under pressure. The pressurized medical liquid is provided to a patient through the conduit means similar to the elastomeric bladder type device.

A particular problem in the infusion devices in the art is achieving a relatively constant flow rate for the infusion of the liquid. The relatively constant flow rate is particularly important when infusion over extended periods of time, such as 24 or 48 hours, is required for the drug therapy. In the infusion devices utilizing elastomeric bladders, such relatively constant flow rates have been achieved by means such as prestressing the elastomeric bladder and the use of costly bladder material. The use of such additional prestress housing and expensive bladder material, of course, adds to the costs of such disposable infusers. In the syringe-type infusion devices, the rate of infusion is restricted to a relatively short period of time because of the accuracy problem found in such designs.

What would thus be desirable would be a disposable infuser device which is able to give relatively constant flow rates over extended periods of infusing while maintaining a comparatively low manufacturing and materials cost factor. The present invention achieves these requirements.

SUMMARY OF THE INVENTION

The present invention provides a syringe-type disposable infusion device having as a biasing source a vacuum. The present device includes a liquid chamber which in a preferred embodiment is a cylindrical barrel. At one end of the cylindrical barrel, a plug is fixed in housing which includes an aperture that extends through the plug. A conduit is connected to the exterior plug aperture to define a dispensing passageway for transporting the liquid from the liquid chamber to the infusion site of the patient. A flow regulator is disposed somewhere in the dispensing passageway for permitting the liquid to flow from the liquid chamber to the dispensing passageway and at a predetermined rate into the patient.

At the opposite end of the cylindrical barrel, a liquid plunger is provided in sliding sealing engagement with the interior surface of the liquid chamber. Extending posteriorly from the liquid plunger is an arm.

Additionally provided is at least one source of vacuum or a vacuum chamber. In the preferred embodiment, the vacuum chamber is a cylindrical barrel which is sealed at one end. At the opposite end, a vacuum plunger is provided in sliding sealing engagement with the interior surface of the vacuum chamber. An arm is provided to establish a direct link between the vacuum plunger in the vacuum chamber and the liquid plunger in the liquid chamber.

DETAILED DESCRIPTION OF THE PREFERRED EMBODIMENT

Figure 1:
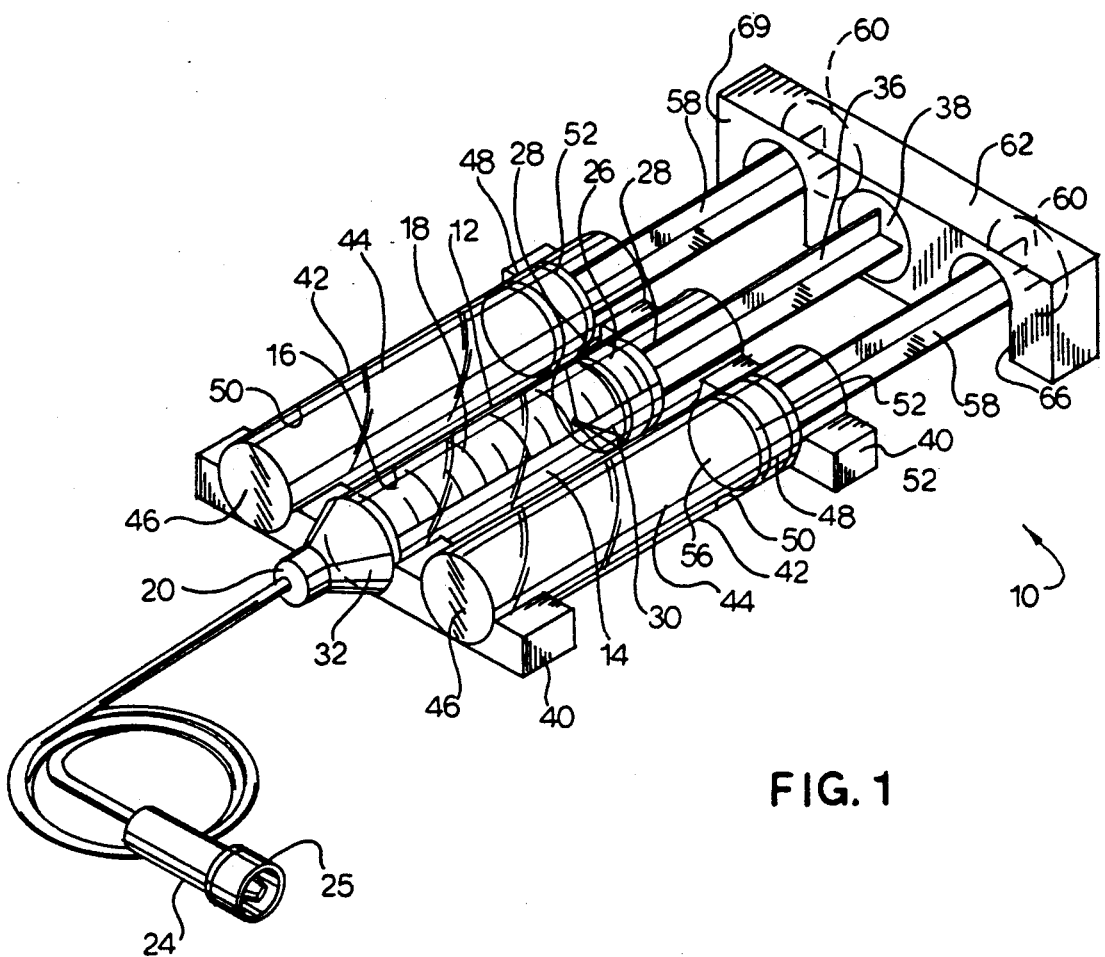
FIG. 1 is a perspective view of an infusion device made in accordance with the principles of the present invention.

Referring first to FIG. 1, a perspective view is seen wherein a device made in accordance with the principles of the present invention is designated generally by the reference number 10. The device 10 includes a first tubular housing defining a rigid cylindrical barrel 12. The rigid cylindrical barrel 12 defines a tubular liquid chamber 14 which includes an interior 16. The rigid cylindrical barrel 12 is preferably molded of a transparent material such as plastic to enable clear visual inspection of the interior 16 of the liquid chamber 14. Imprinted, inscribed or otherwise applied to the barrel wall, a graduated volume scale 18 is also preferably provided.

Sealingly attached to the anterior end of the liquid chamber 14 is a plug housing 20. The plug housing 20 defines an access aperture extending therethrough which establishes fluid communication with the liquid chamber interior 16. Also sealingly attached to the plug housing 20 is a fluid conduit which includes tubing 22. The tubing 22 includes a proximal end and a distal end. Secured on the distal end of the tubing 22 in fluid communication with the interior of the tubing 22 is a flow restrictor 24. In a preferred embodiment, the flow restrictor 24 is a glass capillary tube. The flow restrictor 24 can be contained in housing which can preferably include a luer connector 25 for connection to a catheter (not shown) having a cooperative luer connector.

The tubing 22 proximal end is secured to the plug with the interior of the tubing 22 in fluid communication with the access aperture. While the tubing 22 can be permanently secured to the plug housing 20 by adhesive or the like, in a preferred embodiment the tubing 22 can be disconnectable from the plug housing 20. A preferred embodiment of such detachable connector will be described in detail below.

A liquid plunger 26 is contained within the liquid chamber 14. The liquid plunger 26 includes a pair of outwardly projecting ribs 28 which are sized and shaped to establish a sliding, sealing engagement with the interior surface 16 of the barrel 12. The outwardly projecting ribs 28 of the liquid plunger 26 are preferably formed integrally with the liquid plunger 26 and can preferably be made of a polypropylene coated rubber, silicon rubber, coated neoprene, or a similar type of material to provide a sealing, sliding engagement while minimizing the friction between the liquid plunger 26 and the interior surface 16 of the barrel 12. Additionally, the anterior surface 30 of the liquid plunger 26 exposed to the interior 16 of the liquid chamber 14 is preferably formed in a conical shape which cooperates with the conically shaped housing 32 at the anterior end of the liquid chamber 14 to form a sealing engagement when the liquid chamber 14 is empty. This insures that substantially all of the liquid in the liquid chamber 14 is expressed out of the liquid chamber 14 during infusion.

Provided extending from the posterior side of the liquid plunger 26 is a plunger arm 36. Provided at the posterior periphery of the plunger arm 36 is an enlarged diameter protrusion which defines a plunger head 38.

Additionally provided and secured to the tubular liquid chamber 14 by connector means 40 is at least one additional tubular housing again having a rigid cylindrical barrel 42. This second rigid cylindrical barrel 42 defines a tubular vacuum chamber 44 having an interior surface 50. Again, the second rigid cylindrical barrel is preferably molded of a transparent material such as plastic to enable clear visual inspection of the interior of the vacuum chamber 44. While in the preferred embodiment depicted herein, two vacuum chambers 44 are provided, the present invention contemplates any number of vacuum chambers, from one to more than two, which can then be utilized in combination to provide different forces on the liquid as explained in detail below.

The anterior end of the vacuum chamber 44 includes housing 46 which seals the vacuum chamber 44. This anterior housing 46 is preferably flat to reduce the surface area exposed to the interior of the vacuum chamber 44 to the smallest possible amount. Additionally provided in the vacuum chamber 44 is a vacuum plunger 48. The vacuum plunger 48 includes a pair of outwardly projecting ribs 52 which are sized and shaped to establish a sliding, sealing engagement with the interior surface 50 of the vacuum chamber 44. Again, the outwardly projecting ribs 52 of the vacuum plunger 48 can be preferably made of a polypropylene coated rubber, silicon rubber, coated neoprene or a similar type of material to provide a sliding, sealing engagement while minimizing the friction between the plunger 48 and the interior surface 50 of the vacuum chamber 44. Unlike the liquid plunger 26, the vacuum plunger 48 includes at its anterior end facing the interior of the vacuum chamber 44 a flat surface 56 to reduce the surface area of the vacuum plunger 48 exposed to the vacuum within the vacuum chamber 44. Provided extending from the posterior side of the vacuum plunger 48 is a plunger arm 58. Provided at the posterior periphery of the plunger arm 58 is a plunger head 60.

Because of the characteristics of the vacuum which provides the bias to provide a pressurized source of liquid, an essentially constant force is applied on the vacuum plunger 48 throughout the length of the vacuum chamber 44. This constant force results from the atmospheric pressure which provides a force on the posterior of the vacuum plunger 48 which is a constant force depending on the atmospheric pressure to which the device is exposed. Because a vacuum is contained on the anterior of the vacuum plunger 48, a nearly constant force of approximately zero is applied to the anterior of the vacuum plunger 48 throughout the length of the vacuum chamber 44. It is thus seen that throughout the length of the vacuum chamber 44 approximately constant forces are applied both anteriorly and posteriorly to the vacuum plunger 48.

However, because nature does not know a perfect vacuum, a small amount of force is applied on the anterior end of the vacuum plunger 48. Throughout most of the length of the vacuum chamber 44, this small amount of force is sufficiently "diluted" by the larger "amount" of vacuum to result in a negligible force on the vacuum plunger 48. As the vacuum plunger 48 approaches the closed end 46 of the vacuum chamber 44, the percentage of the evacuated area which is a "perfect" vacuum declines while the area of the evacuated area which is a "force" increases. This results in a logarithmic pressure spike applied to the anterior of the vacuum plunger 44 near the closed end 46 of the vacuum chamber 44. This pressure spike works to offset the atmospheric pressure on the posterior side of the vacuum plunger 48 which results in a drop in the biasing force on the vacuum plunger 48.

Figure 2:
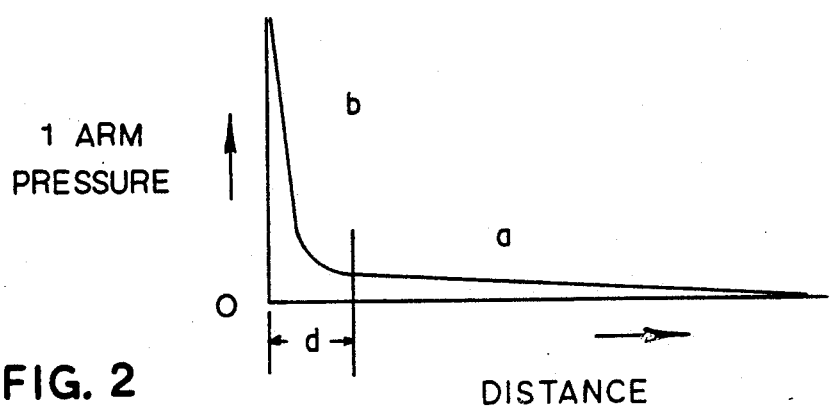
FIG. 2 is a graph of the pressure exerted on the vacuum plunger of the device of FIG. 1 as a function of the position of the vacuum plunger.

Referring to FIG. 2, the forces applied on the anterior end of the vacuum plunger 48 are seen as a function of the distance along the vacuum chamber 44 that the vacuum plunger 48 travels. It is seen that throughout most of this distance a relatively constant, extremely small force (a) is applied which results in a near constant infusion of the liquid. It is further seen that near the area where the vacuum plunger 48 approaches the closed end 46 of the vacuum chamber 44, the force applied on the anterior of the vacuum plunger 48 spikes upwardly (b) and approaches atmospheric pressure.

While this phenomena has been recognized in the art, attempts to eliminate this phenomena have not been satisfactory which has resulted in a lack of commercialized infusers utilizing a vacuum source as a biasing means. The attempts in the prior art to reckon with this phenomena are primarily attempts to perfect the vacuum contained in the evacuated area in an attempt to minimize this pressure spike. While these attempts to perfect a vacuum are theoretically possible, in practice such perfection of the vacuum source quickly results in manufacturing techniques such as manufacturing in a vacuum which are cost prohibitive to a disposable infuser. The present device 10 employs means for preloading the vacuum which prevents this force from resulting in inaccurate infusion.

The vacuum plunger 48 is connected to the liquid plunger 26 by means of a removable support 62 which extends between the vacuum plunger arm 58 and the liquid plunger arm 36. Thus, between the vacuum plunger 48 and the liquid plunger 26, a generally U-shaped arm extends to transfer the force exerted on the vacuum plunger 48 to the liquid plunger 26 to create in the liquid chamber 14 a source of pressurized liquid. While in the presently depicted embodiment, this connection is generally U-shaped, the present invention, of course, contemplates the use of functionally equivalent shaped arm and plunger orientations which result in a functional equivalent to the present device.

Figure 3:
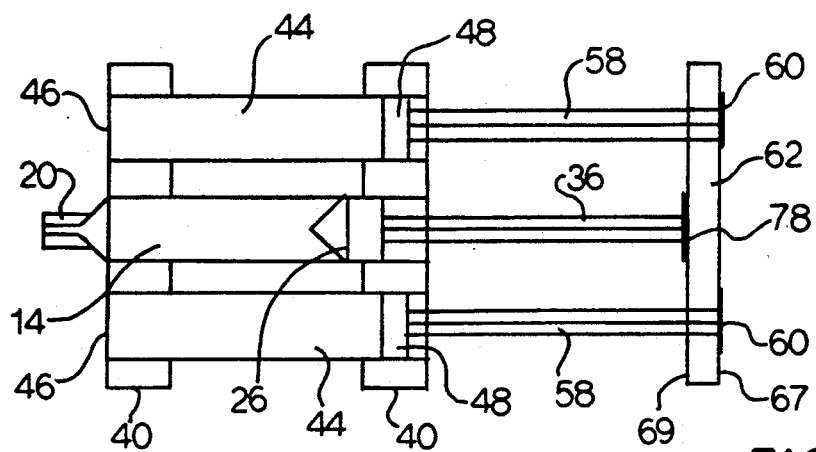
FIG. 3 is an overhead view of the device of FIG. 1 in the loaded position.
Figure 4:
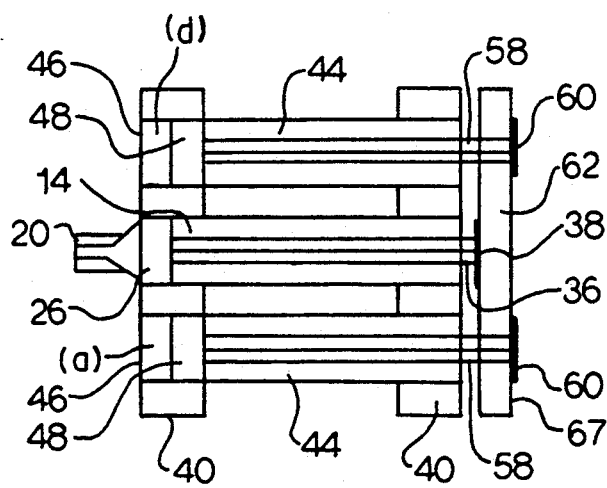
FIG. 4 is an overhead view of the device of FIG. 1 in the unloaded position.
Figure 5:
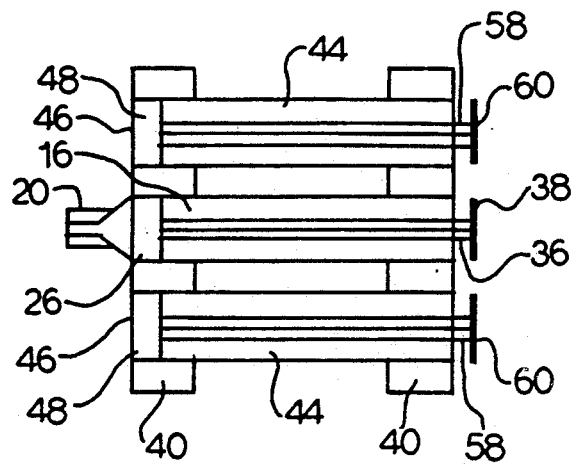
FIG. 5 is an overhead view of the device of FIG. 1 in the storage position.

Referring now to FIGS. 3, 4 and 5, overhead views of the device of FIG. 1 are seen. As is seen particularly in FIGS. 3 and 4, the liquid plunger 26 is offset posteriorly from the vacuum plunger 48 a distance (d). As is seen particularly in FIG. 4, this offset distance (d) results in the liquid plunger 26 abutting against the anterior housing 20 of the liquid chamber 14 before the vacuum plunger 48 abuts against the closed end 46 of the vacuum chamber 44. This distance (d) is referred to herein as the preload distance. Referring to FIG. 2, this preload distance (d) is calculated to allow infusion to be completed before the vacuum plunger 48 approaches the pressure spike applied on the anterior portion of the vacuum plunger 48. Thus, by utilizing this preload distance (d), the rate of infusion is seen to be relatively constant throughout the entire infusion.

Referring now to FIG. 5, the application of this preload distance (d) on the device is described. The device is seen in storage in which the vacuum plunger 48 as well as the liquid plunger 26 is abutted against the anterior of the respective chambers 14, 44. Thus, when in storage in this position, no vacuum or bias is applied to the vacuum plunger 48 and thus the achieved purity of the vacuum is assured during storage and shipping.

Prior to use of the device 10, the removable support 62 is attached to complete the generally U-shaped arm between the vacuum plunger 48 and the liquid plunger 26. The removable support 62 includes at least one slot 66 (best seen in FIG. 1), the specific number of which correspond to the specific number of vacuum chambers 44, and defines a posterior 67 and anterior surface 69.

Prior to use, the removable support 62 is slid over the vacuum plunger arm 58. The size of the slot 66 is sufficiently large to slide over the vacuum plunger arm 58 but is smaller than the diameter of the plunger head 60. Thus, the vacuum plunger head 60 abuts against the posterior surface 67 of the removable support 62.

The removable support 62 is oriented such that the plunger head 38 of the liquid plunger arm 36 abuts against the anterior surface 69 of the removable support 62. Thus, when the removable support 62 is attached to the device 10, the distance between the vacuum plunger arm 67 and the liquid plunger arm 36 is established as the thickness of the removable support 62. The removable support 62 in conjunction with the plunger arms 36, 58 and plunger heads 38, 60 act as means for applying to an unloaded device a preload to the vacuum source. To then load the infuser, a liquid containing a beneficial agent dispersed therein is added under pressure to the liquid chamber 14, the force of which draws the vacuum plunger 48 posteriorly and results in a source of pressurized liquid in the liquid chamber 14.

Because nature does not know a perfect vacuum, the vacuum plunger 26 will never freely abut against the closed end 46 of the vacuum chamber 44. The small distance at which the vacuum plunger 26 comes to rest from the closed end 46 of the vacuum chamber 44 is referred to as a tolerance distance (t). This tolerance distance (t) depends on the purity of the vacuum achieved.

The amount of preload distance (d) needed to assure desired accuracy of infusion can be determined as a function of the tolerance distance (t). Initially, we know at any given distance of the vacuum plunger 48 along the vacuum chamber 44, the forces exerted on the anterior and posterior surface of the vacuum plunger 48 must be equal. Since f=PV, where P is pressure, V is volume, and f is force, it is known:

$$P_1 V_1 = P_2 V_2 \tag{1}$$

where $P_1$ is the pressure exerted on the posterior surface of the vacuum plunger 48, $P_2$ is the pressure exerted on the anterior surface of the vacuum plunger 48. $V_1$ is the volume of the vacuum chamber 44 posterior to the vacuum plunger 48, and $V_2$ is the volume of the evacuated portion of the vacuum chamber 44.

It is also known that $V=(\pi D^2/4)(h)$ for a cylinder where D is the diameter and h is the height of the cylinder. Further, the height of the vacuum chamber 44 as a whole is x+t where x is the length the vacuum plunger travels. Substituting into equation (1), $$P_1(\pi D^2/4)(t) = P_2(\pi D^2/4)(t + x) \tag{2}$$

$$\text{solving for } P_2: \quad P_2 = \frac{P_1(\pi D^2/4)(t)}{(\pi D^2/4)(t + x)} \tag{3}$$

$$\text{cancelling:} \quad P_2 = \frac{P_1(t)}{(t + x)}$$

Further, we can assume that $P_1$ is at atmospheric pressure or 14.6960 psig. Utilizing various values for x and t, we obtain the following values of $P_2$ in psig:

TABLE 1

VERIFICATION OF PRESSURE CHANGE WITH PISTON TRAVEL

FORMULA IS $P_2 = P_1(t)/(t + x)$

| DISTANCE x in inches | DISTANCE t in inches | | | | |
|---|---|---|---|---|---|
| | 0.001 | 0.002 | 0.005 | 0.01 | 0.02 |
| 3.0 | 0.005 | 0.010 | 0.024 | 0.049 | 0.097 |
| 2.0 | 0.007 | 0.015 | 0.037 | 0.073 | 0.146 |
| 1.5 | 0.010 | 0.020 | 0.049 | 0.097 | 0.193 |
| 1.0 | 0.015 | 0.029 | 0.073 | 0.146 | 0.288 |
| 0.5 | 0.029 | 0.059 | 0.146 | 0.288 | 0.565 |
| 0.2 | 0.073 | 0.146 | 0.358 | 0.700 | 1.336 |
| 0.1 | 0.146 | 0.288 | 0.700 | 1.336 | 2.449 |

Thus, when the vacuum plunger 48 is at various distances (x) along the length of the vacuum chamber 44, the evacuated portion exhibits the following degree of vacuum:

TABLE 2

| DISTANCE x in inches | DEGREE OF VACUUM* | | | | |
|---|---|---|---|---|---|
| | DISTANCE t in inches | | | | |
| | 0.001 | 0.002 | 0.005 | 0.01 | 0.02 |
| 3.0 | 99.97% | 99.93% | 99.83% | 99.67% | 99.34% |
| 2.0 | 99.95% | 99.90% | 99.75% | 99.50% | 99.01% |
| 1.5 | 99.93% | 99.87% | 99.67% | 99.34% | 98.68% |
| 1.0 | 99.90% | 99.80% | 99.50% | 99.01% | 98.04% |
| 0.5 | 99.80% | 99.60% | 99.01% | 98.04% | 96.15% |
| 0.2 | 99.50% | 99.01% | 97.56% | 95.24% | 90.91% |
| 0.1 | 99.01% | 98.04% | 95.24% | 90.91% | 83.33% |

*100% represents absolute vacuum

By utilizing these values, the desired degree of accuracy can be achieved by knowing the tolerance of manufacture as well as the length of the vacuum chamber 44. For example, if a tolerance of between 0.001 to 0.002 inches is achieved and an accuracy of ±5% is desired, approximating from TABLE 2, a preload distance of greater than 0.5 inches is required.

Additionally, as is seen the force executed as the vacuum plunger 48 is dependent on the atmospheric pressure executed on the device 10. To understand how differences in the atmospheric pressure could affect the present device 10, atmospheric conditions were obtained from The National Weather Service for the following sample cities:

TABLE 3

| | ATMOSPHERIC CONDITIONS | | | |
|---|---|---|---|---|
| | Boston | Los Angeles | Chicago | Denver |
| ELEV* | 15 ft. | 270 ft. | 658 ft. | 5,283 ft. |
| PRESSURE** | | | | |
| MAX | 1.036 | 1.019 | 1.032 | .843 |
| MIN | .948 | .975 | .956 | .792 |
| AVG | 1.001 | .997 | .980 | .823 |
| RANGE*** MID | ±4.4% | ±2.2% | ±3.8% | ±3.1% |

*Above sea level
**In Atmos
***In percentages

It is thus seen that the changes in atmospheric pressure in a given sample city results in a maximum change in biasing pressure of ±4.4%, which is well within a satisfactory tolerance range of infusion. Additionally, differences in average atmospheric pressure for different geographic areas can simply be compensated by adjusting the concentration of beneficial agent in the medical liquid by a pharmacist.

Figure 6:
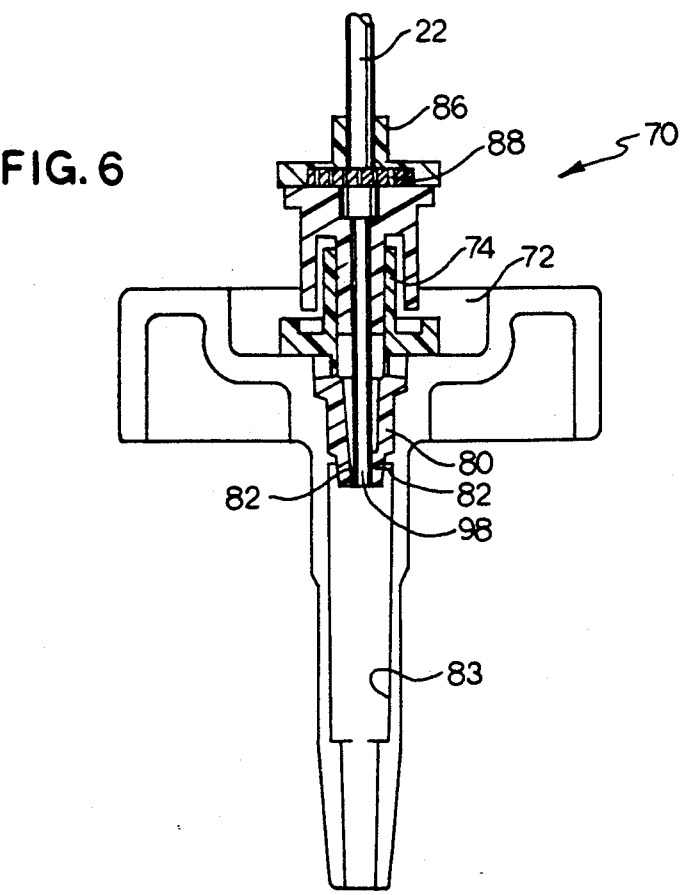
FIG. 6 is a cross-sectional view of a preferred embodiment of a two-way valve made in accordance with the principles of the present invention.
Figure 7:
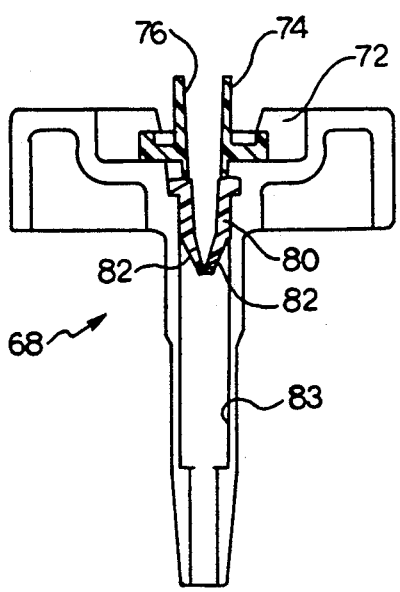
FIG. 7 is a cross-sectional view of connector housing of the device of FIG. 6.
Figure 8:
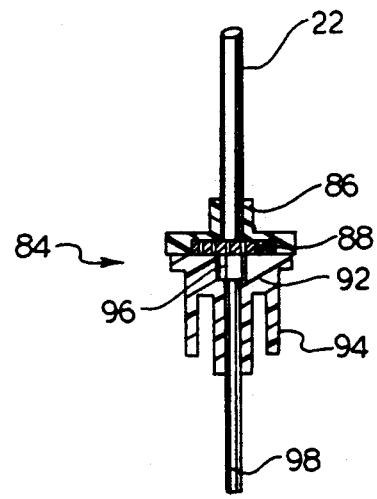
FIG. 8 is a cross-sectional view of attachment housing of the device of FIG. 6.

Referring now to FIGS. 6 through 8, the preferred embodiment of valve means 70 contained in the plug housing 20 of the liquid chamber 14 is seen. Referring first to FIG. 7, a plug portion 68 of the valve means 70 in the loading or storage mode is seen. The valve includes a connector housing 72 which defines a connector 74. The connector can preferably be a female luer. The female luer includes an aperture 76 defined therein which is in fluid communication with a duck-bill valve 80. The duck-bill valve 80 includes a pair of lips 82. Contained on the downstream side of the duck-bill valve 80 is an access aperture 83 which is in liquid communication with the interior of the liquid chamber 14. Thus, to load the liquid chamber 14, a device such as a syringe capable of providing liquid under pressure and having a cooperating connector such as a male luer is attached to the female luer and the liquid contained within the syringe is expressed under pressure past the duck-bill valve 80 to the interior of the liquid chamber 14 to define a source of pressurized liquid. After loading, the duck-bill valve 80 contains the liquid under pressure within the liquid chamber 14.

Referring now to FIG. 8, an outlet conduit 84 of the valve means 70 is seen in detail. The tubing 22 is secured to a filter housing 86 contained on the outlet conduit 84 by means such as an adhesive. The filter housing 86 defines a filter aperture which contains a filter 88 in fluid communication with the interior of the tubing 22. The filter 88 is utilized to prevent non-dissolved beneficial agent contained in the medical liquid from entering the fluid conduit and thus the venous system of the patient. The filter 88 can be preferably made of stainless steel, platinum wire, or other suitable material or of any of a variety of polymers such as polytetrafluoroethylene, having a porous or multifilament configuration capable of operating as a screen and which will be substantially unreactive in the presence of the beneficial agent.

The outlet conduit 84 further includes housing 92 which defines a connector 94 which acts cooperatively with the connector 74 on the plug portion 68. In the preferred embodiment, this cooperating connector 94 is a male luer. The housing further defines an aperture 96 in fluid communication with the filter 88. Extending from the aperture 96 is a blunt cannula 98 defining an internal channel in fluid communication with the aperture 96.

The blunt cannula 98 extends a distance from the housing 92 which is defined by the duck-bill valve 80. Specifically, The blunt cannula 98 must extend sufficiently from the housing 92 to open the duck-bill valve 80 when the connectors 74, 94 are secured. While extending the blunt cannula 98 past the duck-bill valve 80 does satisfactorily open the duck-bill valve 80, it has been found that such extension results in an amount of leakage of the liquid stored in the liquid chamber 14 proportional to the distance past the duck-bill valve 80 that the blunt cannula 98 extends.

Thus, in a preferred embodiment, the blunt cannula 98 extends into the duck-bill valve 80 sufficiently to separate the lips 82 of the duck-bill valve 80 without penetrating through. In a further preferred embodiment, the outer periphery of the diluent cannula 98 is about flush with the end of the duck-bill valve 80. In this embodiment, small manufacturing tolerances will not appreciably affect the performance of the valve as sufficient penetration is assured to separate the lips 82 but extensive leakage is prevented.

After loading, to use the device 10, the male luer is connected to the female luer. This forces the blunt cannula 98 into engagement with the duck-bill valve 80. When the male luer and female luer are secured, the open end of the blunt cannula 98 extends into the duck-bill valve 80 to establish fluid communication with the interior of the liquid chamber 14 (best seen in FIG. 6). Thus, the liquid under pressure in the liquid chamber 14 rushes into the blunt cannula 98, past the filter 88, into the tubing 22, and past the flow restrictor 24 contained in the tubing 22 to the patient.

It should be understood that various changes and modifications to the preferred embodiments described herein will be apparent to those skilled in the art. Such changes and modifications can be made without departing from the spirit and scope of the present invention and without diminishing its attendant advantages. It is, therefore, intended that such changes and modifications be covered by the appended claims.

What is claimed is:

1. A device for infusing liquid comprising:
   a liquid chamber adapted to receive a liquid under pressure, the liquid chamber having a liquid plunger contained within the liquid chamber and a fluid conduit extending from the liquid chamber;
   a vacuum chamber, the vacuum chamber having a vacuum plunger contained within the vacuum chamber;
   an arm connecting the liquid plunger and the vacuum plunger such that when liquid is introduced into the liquid chamber under pressure the vacuum plunger biases; and
   means for preloading the vacuum plunger such that the vacuum plunger does not abut an end of the vacuum chamber housing after infusion.

2. The device of claim 1 further wherein the preload means can be disabled such that the device can be stored without a preload.

3. The device of claim 1 wherein the liquid chamber is tubular.

4. The device of claim 1 wherein the vacuum chamber is tubular.

5. The device of claim 1 wherein the liquid plunger further includes a plunger arm, the vacuum plunger further includes a plunger arm, and a removable support connects the plunger arms thus forming a generally U-shaped arm.

6. The device of claim 5 wherein the removable support offsets the liquid plunger from the vacuum plunger the preload distance thereby acting as the preload means.

7. An infusion device comprising:
   a tubular housing for receiving a liquid having at one end an outlet aperture;
   a liquid plunger slidably mounted in the liquid tubular housing;
   at least one tubular housing having a closed end defining a vacuum chamber;
   a vacuum plunger slidably mounted in the closed end tubular housing;
   an arm connecting the liquid plunger and the vacuum plunger such that when liquid is introduced under pressure in the liquid tubular housing via the outlet aperture the vacuum plunger biases; and
   means for preloading the vacuum plunger such that upon expulsion of the liquid from the liquid tubular housing the vacuum plunger is a preload distance from the closed end of the vacuum housing.

8. The device of claim 7 further wherein the preload means can be disabled such that the device can be stored without a preload.

9. The device of claim 7 wherein the liquid plunger further includes a plunger arm, the vacuum plunger further includes a plunger arm, and a removable support connects the plunger arms thus forming a generally U-shaped arm.

10. The device of claim 9 wherein the removable support offsets the liquid plunger from the vacuum plunger the preload distance thereby acting as the preload means.

* * * * *